(12) United States Patent
Thompson et al.

(10) Patent No.: US 10,828,135 B2
(45) Date of Patent: *Nov. 10, 2020

(54) SYSTEMS AND PROCESSES FOR FORMING ANATOMICAL FEATURES IN DENTURES

(71) Applicant: Global Dental Science LLC, Scottsdale, AZ (US)

(72) Inventors: Timothy C. Thompson, Fountain Hills, AZ (US); Scott C. Keating, Louisville, CO (US); Andrzej J. Jakson, Amherst, NY (US)

(73) Assignee: Global Dental Sciences, LLC, Scottsdale, AZ (US)

( * ) Notice: Subject to any disclaimer, the term of this patent is extended or adjusted under 35 U.S.C. 154(b) by 785 days.

This patent is subject to a terminal disclaimer.

(21) Appl. No.: 14/798,717

(22) Filed: Jul. 14, 2015

(65) Prior Publication Data

US 2015/0327961 A1 Nov. 19, 2015

Related U.S. Application Data

(63) Continuation of application No. 13/823,621, filed as application No. PCT/US2011/059230 on Nov. 3,
(Continued)

(51) Int. Cl.
*A61C 13/10* (2006.01)
*G16H 20/40* (2018.01)
(Continued)

(52) U.S. Cl.
CPC .......... *A61C 13/10* (2013.01); *A61C 13/0004* (2013.01); *G16H 20/40* (2018.01); *A61C 9/004* (2013.01); *Y10T 29/49567* (2015.01)

(58) Field of Classification Search
CPC .............................................. A61C 13/00–225
See application file for complete search history.

(56) References Cited

U.S. PATENT DOCUMENTS

| 200,445 A | 2/1878 | Fahnestock |
| 321,847 A | 7/1885 | Peirce et al. |

(Continued)

FOREIGN PATENT DOCUMENTS

| CA | 2505892 | 5/2004 |
| CN | 1750797 | 3/2006 |

(Continued)

OTHER PUBLICATIONS

EP Application No. 17191917.8—European Search Report dated May 22, 2018.
(Continued)

*Primary Examiner* — Yogesh P Patel
(74) *Attorney, Agent, or Firm* — Harvey Law; Derrick Harvey

(57) ABSTRACT

The system of a preferred embodiment uses a process whereby a true replication of the patient's jaw structure is created in a digital three dimensional model. This true replication is then used to precisely locate and/or copy the anatomical landmarks of the patient for use in fabricating a denture base for use in a denture for the individual patient. This system is able to create a denture with precisely located features corresponding to the anatomical landmarks of the patient with little manual intervention.

7 Claims, 11 Drawing Sheets

Related U.S. Application Data 2011, now Pat. No. 9,155,599, which is a continuation-in-part of application No. 12/939,138, filed on Nov. 3, 2010, now Pat. No. 9,402,698.

(51) Int. Cl.
*A61C 13/00* (2006.01)
*A61C 9/00* (2006.01)

(56) References Cited

U.S. PATENT DOCUMENTS

| | | |
|---|---|---|
| 711,324 A | 10/1902 | Lacy |
| 830,887 A | 9/1906 | Robert |
| 1,223,450 A | 4/1917 | Van Allen |
| 1,293,627 A | 2/1919 | Bowers |
| 1,585,348 A | 5/1926 | Hick et al. |
| 1,652,910 A | 12/1927 | Psayla |
| 1,714,185 A | 5/1929 | Hugh |
| 1,863,591 A | 6/1932 | Crowell |
| 1,914,606 A | 6/1933 | Kinna et al. |
| 2,036,678 A | 4/1936 | White |
| 2,107,181 A * | 2/1938 | Guyton ............... A61C 13/04 433/199.1 |
| 2,398,671 A | 4/1946 | Saffir |
| 2,418,833 A | 4/1947 | Harris et al. |
| 2,472,492 A | 6/1949 | Saffir |
| 2,514,076 A | 7/1950 | Kelly |
| 2,602,997 A | 7/1952 | Clawson |
| 2,641,835 A | 6/1953 | Greenmun |
| 2,985,961 A | 5/1961 | Schwartz |
| 2,994,957 A | 8/1961 | Mcleod |
| 3,083,459 A | 4/1963 | McMurry et al. |
| 3,126,429 A | 3/1964 | Saffir |
| 3,241,238 A | 3/1966 | Kersten |
| 3,335,495 A | 8/1967 | Theodore |
| 3,458,936 A | 8/1969 | Tuccillo et al. |
| 3,470,614 A | 10/1969 | Kelly |
| 3,518,761 A | 7/1970 | Susman et al. |
| 3,644,996 A | 2/1972 | Weinkle |
| 3,667,123 A | 6/1972 | Huey |
| 3,702,027 A | 11/1972 | Marshall et al. |
| 3,727,309 A | 4/1973 | Huey |
| 3,748,739 A | 7/1973 | Thibert |
| 3,813,777 A | 6/1974 | VanHandel et al. |
| 3,839,796 A | 10/1974 | Hazer |
| 3,844,702 A | 10/1974 | Dimmer et al. |
| 3,846,911 A | 11/1974 | Wichner |
| 3,908,272 A | 9/1975 | Arnold |
| 3,937,773 A | 2/1976 | Huffman |
| 3,987,546 A | 10/1976 | Trampe |
| 4,029,632 A | 6/1977 | Gross et al. |
| 4,115,488 A | 9/1978 | Colpitts |
| 4,184,253 A * | 1/1980 | Tureaud ............... A61C 13/00 433/171 |
| 4,227,877 A | 10/1980 | Tureaud et al. |
| 4,247,287 A | 1/1981 | Gigante |
| 4,299,573 A | 11/1981 | Ricci |
| 4,398,834 A | 8/1983 | Huffman |
| 4,533,325 A | 8/1985 | Blair |
| 4,575,340 A | 3/1986 | Lustig |
| 4,591,341 A | 5/1986 | Andrews |
| 4,634,377 A | 1/1987 | Behrend |
| 4,784,608 A | 11/1988 | Mays |
| 4,931,016 A | 6/1990 | Sillard |
| 2,030,102 A | 7/1991 | Lang |
| 5,043,199 A | 8/1991 | Kubota et al. |
| 5,098,296 A | 3/1992 | Cullen |
| 5,151,044 A | 9/1992 | Rotsaert |
| 5,169,309 A | 12/1992 | Staubli et al. |
| 5,188,529 A | 2/1993 | Luth |
| 5,234,339 A | 8/1993 | Grigersit |
| 5,427,906 A | 6/1995 | Hanson |
| 5,452,219 A | 9/1995 | Dehoff et al. |
| 5,672,305 A | 9/1997 | Kogure |
| 5,676,546 A | 10/1997 | Heitmann et al. |
| 5,711,668 A | 1/1998 | Huestis |
| 5,716,214 A | 2/1998 | Lund |
| 5,718,584 A | 2/1998 | Wong |
| 5,730,825 A | 3/1998 | Atake |
| 5,775,899 A | 7/1998 | Huffman |
| 5,833,461 A | 11/1998 | Wong |
| 5,839,900 A | 11/1998 | Billet et al. |
| 5,885,078 A | 3/1999 | Cagna et al. |
| 5,934,906 A | 8/1999 | Phimmasone |
| 5,985,170 A | 11/1999 | Inaba et al. |
| 6,030,218 A | 2/2000 | Robinson |
| 6,056,547 A | 5/2000 | Names |
| 6,116,070 A | 9/2000 | Oshirio |
| 6,126,445 A | 10/2000 | Wilioughby |
| 6,139,322 A | 10/2000 | Liu |
| 6,149,427 A | 11/2000 | Van Handel |
| 6,224,372 B1 | 5/2001 | Ibsen et al. |
| 6,227,851 B1 | 5/2001 | Chishti |
| 6,257,895 B1 | 7/2001 | Oestreich |
| 6,384,107 B2 | 5/2002 | Liu |
| 6,422,864 B1 | 7/2002 | Glatt |
| 6,488,503 B1 | 12/2002 | Lichkus et al. |
| 6,616,444 B2 | 9/2003 | Andreiko et al. |
| 6,788,986 B1 | 9/2004 | Traber et al. |
| 6,814,575 B2 | 11/2004 | Piorier |
| 6,851,949 B1 | 2/2005 | Sachdeva |
| 7,021,934 B2 | 4/2006 | Aravena |
| 7,153,135 B1 | 12/2006 | Thomas |
| 7,234,940 B2 | 6/2007 | Weissman |
| 7,433,810 B2 | 10/2008 | Pavloskaia et al. |
| 7,474,932 B2 | 1/2009 | Geng |
| 7,530,810 B2 | 5/2009 | Clement |
| 7,653,455 B2 | 1/2010 | Cinader, Jr. |
| 7,704,076 B2 | 4/2010 | Mullaly |
| 7,758,345 B1 | 7/2010 | Christensen |
| 7,758,346 B1 | 7/2010 | Letcher |
| 7,806,691 B2 | 10/2010 | Berger |
| 7,854,611 B2 | 12/2010 | Yau et al. |
| 7,901,209 B2 | 3/2011 | Saliger et al. |
| 7,909,607 B2 | 3/2011 | Yau et al. |
| 7,943,068 B2 | 5/2011 | Panzera |
| 7,950,924 B2 | 5/2011 | Brajnovic |
| 8,043,091 B2 | 10/2011 | Schmitt |
| 8,348,669 B1 | 1/2013 | Schmitt |
| 8,567,408 B2 | 10/2013 | Roettger |
| 8,641,938 B2 | 2/2014 | Howe |
| 8,801,431 B2 | 8/2014 | Thompson et al. |
| 8,875,398 B2 | 11/2014 | Balshi et al. |
| 9,055,993 B2 | 6/2015 | Grobbee et al. |
| 9,155,599 B2 * | 10/2015 | Thompson ......... A61C 13/0004 |
| 9,192,456 B2 | 11/2015 | Howe |
| 9,213,784 B2 | 12/2015 | Thompson et al. |
| 9,364,302 B2 | 6/2016 | Thompson et al. |
| 9,402,698 B2 * | 8/2016 | Thompson ........... A61C 9/0046 |
| 9,468,509 B2 | 10/2016 | Howe |
| 9,492,252 B2 | 11/2016 | Howe |
| 9,717,572 B2 | 8/2017 | Thompsom Et I:A |
| 9,744,010 B2 | 8/2017 | Grobbee |
| 1,020,676 A1 | 2/2019 | Grobbee et al. |
| 1,025,173 A1 | 4/2019 | Grobbee |
| 2002/0015934 A1 | 2/2002 | Rubbert et al. |
| 2002/0180760 A1 | 12/2002 | Rubbert et al. |
| 2003/0108845 A1 | 6/2003 | Giovannone et al. |
| 2003/0138756 A1 | 7/2003 | Monkmeyer |
| 2003/0162147 A1 | 8/2003 | Dequeker |
| 2003/0163291 A1 | 8/2003 | Jordan et al. |
| 2003/0211444 A1 | 11/2003 | Andrews |
| 2004/0005530 A1 | 1/2004 | Mullaly |
| 2004/0029068 A1 | 2/2004 | Sachdeva et al. |
| 2004/0185422 A1 | 9/2004 | Orth et al. |
| 2004/0219490 A1 | 11/2004 | Gartner et al. |
| 2005/0175957 A1 | 8/2005 | Haje et al. |
| 2005/0186539 A1 | 8/2005 | McLean |
| 2005/0284489 A1 | 12/2005 | Ambis |
| 2006/0040232 A1 | 2/2006 | Shoup |
| 2006/0040236 A1 | 2/2006 | Schmitt |
| 2006/0063135 A1 | 3/2006 | Mehl |
| 2006/0210945 A1 | 9/2006 | Savic et al. |
| 2006/0286507 A1 | 12/2006 | Dequeker |

(56) References Cited

U.S. PATENT DOCUMENTS

| | | |
|---|---|---|
| 2007/0009852 A1 | 1/2007 | Childress |
| 2007/0154868 A1 | 7/2007 | Scharlack et al. |
| 2007/0190488 A1 | 8/2007 | Rusler |
| 2007/0190492 A1 | 8/2007 | Schmitt |
| 2007/0231774 A1 | 10/2007 | Massad |
| 2008/0085489 A1 | 4/2008 | Schmitt |
| 2008/0090207 A1 | 4/2008 | Rubbert |
| 2008/0127698 A1 | 6/2008 | Luckey et al. |
| 2008/0206710 A1 | 8/2008 | Kruth et al. |
| 2008/0206714 A1 | 8/2008 | Schmitt |
| 2008/0209974 A1 | 9/2008 | Ewolski et al. |
| 2008/0228303 A1 | 9/2008 | Schmitt |
| 2008/0300716 A1 | 12/2008 | Kopelman |
| 2009/0026643 A1 | 1/2009 | Wiest et al. |
| 2009/0081618 A1 | 3/2009 | Lamar |
| 2009/0143609 A1 | 6/2009 | Araya |
| 2009/0148813 A1 | 6/2009 | Sun et al. |
| 2009/0162813 A1 | 6/2009 | Glor |
| 2009/0181346 A1 | 7/2009 | Orth |
| 2009/0220916 A1* | 9/2009 | Fisker ............. A61C 9/00 433/201.1 |
| 2009/0287332 A1 | 11/2009 | Adusumilli et al. |
| 2009/0291407 A1 | 11/2009 | Kuo |
| 2009/0325125 A1 | 12/2009 | Diangelo et al. |
| 2010/0015572 A1 | 1/2010 | Dirkes et al. |
| 2010/0040997 A1* | 2/2010 | Kadobayashi ....... A61C 13/097 433/191 |
| 2010/0062394 A1 | 3/2010 | Jones et al. |
| 2010/0086186 A1 | 4/2010 | Zug et al. |
| 2010/0094446 A1 | 4/2010 | Baloch et al. |
| 2010/0105011 A1 | 4/2010 | Karkar et al. |
| 2010/0324875 A1 | 12/2010 | Kalili |
| 2011/0045442 A1* | 2/2011 | Adusimilli ............ A61C 9/00 433/201.1 |
| 2011/0112804 A1 | 5/2011 | Chishti et al. |
| 2011/0129796 A1 | 6/2011 | Riggio |
| 2011/0236856 A1 | 9/2011 | Kanazawa et al. |
| 2011/0244417 A1 | 10/2011 | Hilsen et al. |
| 2012/0058449 A1 | 3/2012 | Sklarski et al. |
| 2012/0094253 A1 | 4/2012 | Berger |
| 2012/0095732 A1 | 4/2012 | Fisker et al. |
| 2012/0100500 A1 | 4/2012 | Gao |
| 2012/0178045 A1 | 7/2012 | Massad |
| 2012/0179281 A1 | 7/2012 | Steingart et al. |
| 2012/0258426 A1 | 10/2012 | Boe |
| 2012/0285019 A1 | 11/2012 | Schechner et al. |
| 2012/0315601 A1 | 12/2012 | Fishman et al. |
| 2012/0329008 A1 | 12/2012 | Fishman et al. |
| 2013/0071801 A1 | 3/2013 | Lanfried |
| 2013/0101962 A1* | 4/2013 | Howe ................ A61C 9/0053 433/191 |
| 2013/0108988 A1 | 5/2013 | Simoncic |
| 2013/0167380 A1 | 7/2013 | Balshi |
| 2013/0209962 A1 | 8/2013 | Thompson et al. |
| 2013/0216978 A1 | 8/2013 | Thompson et al. |
| 2013/0218532 A1 | 8/2013 | Thompson et al. |
| 2013/0221554 A1 | 8/2013 | Jung et al. |
| 2013/0249132 A1 | 9/2013 | Thompson et al. |
| 2013/0280672 A1 | 10/2013 | Thompson et al. |
| 2013/0316302 A1 | 11/2013 | Fisker |
| 2013/0337412 A1 | 12/2013 | Kwon |
| 2014/0045967 A1 | 2/2014 | Thomas et al. |
| 2014/0051037 A1 | 2/2014 | Fisker |
| 2014/0080094 A1 | 3/2014 | Howe |
| 2014/0099600 A1 | 4/2014 | Harrison |
| 2014/0234802 A1 | 8/2014 | Howe |
| 2014/0242539 A1 | 8/2014 | Fisker et al. |
| 2014/0255873 A1 | 9/2014 | Bullis et al. |
| 2014/0272777 A1 | 9/2014 | Howe |
| 2014/0272796 A1 | 9/2014 | Grobbee et al. |
| 2014/0272798 A1 | 9/2014 | McDermott |
| 2014/0272800 A1 | 9/2014 | Howe |
| 2015/0010885 A1 | 1/2015 | Balshi et al. |
| 2015/0037760 A1 | 2/2015 | Thompson et al. |
| 2015/0064653 A1 | 3/2015 | Grobbee et al. |
| 2015/0111177 A1 | 4/2015 | Fisker |
| 2015/0132718 A1* | 5/2015 | Kerschensteiner ......... A61C 13/0003 433/196 |
| 2015/0134094 A1 | 5/2015 | Thompson et al. |
| 2015/0182314 A1 | 7/2015 | Morales et al. |
| 2015/0182316 A1 | 7/2015 | Morales et al. |
| 2015/0230891 A1 | 8/2015 | Grobbee et al. |
| 2015/0245891 A1 | 9/2015 | Grobbee |
| 2015/0245892 A1 | 9/2015 | Grobbee |
| 2015/0342711 A1 | 12/2015 | Grobbee |
| 2016/0008108 A1 | 1/2016 | Thompson et al. |
| 2016/0089221 A1 | 3/2016 | Christen et al. |
| 2017/0014212 A1 | 1/2017 | Fischer |
| 2017/0112599 A1 | 4/2017 | Balshi |
| 2017/0325920 A1 | 11/2017 | Ginsburg et al. |
| 2018/0055611 A1 | 3/2018 | Sun |
| 2018/0116771 A1 | 5/2018 | Keating et al. |
| 2019/0105134 A1 | 4/2019 | Cohen |
| 2019/0175317 A1 | 6/2019 | Grobbee |

FOREIGN PATENT DOCUMENTS

| | | |
|---|---|---|
| CN | 104688367 | 6/2015 |
| EP | 1062916 | 12/2000 |
| EP | 1252867 | 10/2002 |
| EP | 2915503 | 7/2016 |
| EP | 3348228 | 7/2018 |
| FR | 2035133 | 12/1970 |
| JP | 2008307281 | 12/2008 |
| WO | 91/07141 | 5/1991 |
| WO | WO 2001032096 | 12/2001 |
| WO | WO 2003024352 | 3/2003 |
| WO | WO 2004060197 | 7/2004 |
| WO | WO2009105661 | 8/2009 |
| WO | WO 2009105700 | 8/2009 |
| WO | 2010/008434 | 1/2010 |
| WO | WO 2010022479 | 3/2010 |
| WO | WO 2012030493 | 3/2012 |
| WO | WO 2012041329 | 4/2012 |
| WO | WO 20/2084655 | 5/2012 |
| WO | WO 2012061652 | 5/2012 |
| WO | WO 2012061659 | 5/2012 |
| WO | WO 2012061660 | 5/2012 |
| WO | WO2014017136 | 7/2014 |
| WO | WO 2014130536 | 8/2014 |
| WO | WO 2014159436 | 10/2014 |
| WO | WO 2015031062 | 3/2015 |

OTHER PUBLICATIONS

European App EP14840991.5—EPO Search Report dated Apr. 19, 2017.

European App EP11838843.8—EPO Search Report dated Mar. 4, 2014.

European App EP11838843.8—EPO Examination dated Sep. 12, 2017.

PCT App Opinion PCTUS2811059230—International Search Report and Written dated Jul. 18, 2012.

PCT App PCTUS2011059230—Preliminary Report on Patentability dated May 8, 2013.

Positioning handle and occlusal locks for the Teeth-in-a-Day protocol:, The Journal of Prosthetic Dentistry, 2016, Balshi et al., p. 274-278.

"A New Dentistry Protocol for Immediate Functional Loading of Dental Implants"Dentistry Today, Balshi et al.., Sep. 2001, vol. 20, No. 9.

U.S. Appl. No. 13/343,566—Restrictriction Requirement dated Apr. 16, 2014.

U.S. Appl. No. 13/343,566—Notice of Allowance dated Jun. 26, 2014.

U.S. Appl. No. 14/013,295—Non-Final Official Action dated Dec. 19, 2014.

U.S. Appl. No. 14/013,295—Notice of Allowance dated Apr. 13, 2015.

(56) References Cited

OTHER PUBLICATIONS

U.S. Appl. No. 14/495,036—Non-Final Official Action dated May 19, 2015.
U.S. Appl. No. 14/495,036—Final Official Action dated Nov. 6, 2015.
U.S. Appl. No. 14/495,036—Final Official Action dated Jun. 4, 2016.
U.S. Appl. No. 14/698,649—Non-Final Official Action dated Sep. 26, 2017.
U.S. Appl. No. 15/191,868—Non-Final Official Action dated Jun. 16, 2017.
U.S. Appl. No. 15/390,330—Non-Final Official Action dated Jun. 1, 2017.
European App EP14774571.5—EPO Search Report dated Aug. 12, 2016.
European App EP1618485.8—EPO Search Report dated Jan. 12, 2017.
U.S. Appl. No. 12/939,138—Non-Final Official Action dated Apr. 9 2015.
U.S. Appl. No. 12/939,138—Final Official Action dated Aug. 19, 2015.
U.S. Appl. No. 12/939,138—Advisory Action dated Nov. 23, 2015.
U.S. Appl. No. 12/939,141—Restriction Requirement dated Apr. 9, 2015.
U.S. Appl. No. 12/939,141—Non-Final Official Action dated Jul. 12, 2016.
U.S. Appl. No. 13/249,210 Non-Final Official Action dated Mar. 6, 2014.
U.S. Appl. No. 13/249,210—Notice of Allowance dated Jun. 6, 2014.
U.S. Appl. No. 13/369,238—Restriction Requirement dated Apr. 16, 2014.
U.S. Appl. No. 13/369,238—Non-Final Official Action dated Sep. 1, 2015.
U.S. Appl. No. 13/369,238—Non-Final Official Action dated Jan. 4, 2016.
U.S. Appl. No. 13/369,238—Notice of Allowance dated Apr. 13, 2015.
U.S. Appl. No. 13/823,621—Restriction Requirement dated Sep. 5, 4014.
U.S. Appl. No. 13/823,621—Non-Final Official Action dated Oct. 4, 2016.
U.S. Appl. No. 13/823,621—Notice of Allowance dated Jun. 22, 2015.
U.S. Appl. No. 13/823,662—Notice of Allowance dated Aug. 24, 2015.
U.S. Appl. No. 13/830,963—Non-Final Official Acton dated Jun. 20, 2014.
U.S. Appl. No. 13/830,963—Final Official Action dated Nov. 7, 2014.
U.S. Appl. No. 13/830,963—Advisory Action dated Feb. 23, 2015.
U.S. Appl. No. 13/830,963—Non-Final Official Action dated Feb. 12, 2015.
U.S. Appl. No. 13/830,963—Non-Final Official Action dated Aug. 13, 2015.
U.S. Appl. No. 13/830,983—Final Official Action dated Feb. 23, 2016.
U.S. Appl. No. 13/830,963—Notice of Allowance dated Oct. 18, 2017.
U.S. Appl. No. 14/195,348—Restriction Requirement dated Jul. 2, 2014.
U.S. Appl. No. 14/195,348—Non-Final Official Action dated Aug. 21, 2014.
U.S. Appl. No. 14/195,348—Final of Action dated Oct. 21, 2014.
U.S. Appl. No. 14/195,348—Non-Final Official Action dated Dec. 19, 2014.
U.S. Appl. No. 14/195,348—Non-Final Official Action dated Aug. 11, 2015.
U.S. Appl. No. 14/195,348—Final Official Action dated Apr. 18, 2016.
U.S. Appl. No. 14/195,348—Non-Final Official Action dated Dec. 30, 2016.
U.S. Appl. No. 14/195,348—Final Official Action dated Aug. 18, 2017.
U.S. Appl. No. 14/506,338—Non-Final Official Action dated Apr. 7, 2017.
U.S. Appl. No. 14/821,097—Restriction Requirement dated Jan. 4, 2016.
U.S. Appl. No. 14/821,097—Non-Final Official Action dated Jun. 28, 2016.
U.S. Appl. No. 14/821,097—Notice of Allowance dated Apr. 20, 2017.
U.S. Appl. No. 12/939,138—Notice of Allowance dated Mar. 14, 2016.
U.S. Appl. No. 12/939,141—Final Official Action dated Jun. 22, 2015.
PCT Application PCTUS2011059235—International Search Report and Written Opinion dated Jul. 18, 2012.
PCT Application PCTUS2011059235—Preliminary Report on Patentability dated May 8, 2013.
PCT Application PCTUS2011059239—International Search Report and Written Opinion dated Jul. 9, 2012.
PCT Application PCTUS2011059239—Preliminary Reporton Patentability dated May 8, 2013.
PCT Application PCTUS2011059240—International Search Report and Written Opinion dated Jul. 18, 2012.
PCT Application PCTUS2011059240—Preliminary Report on Patentability dated May 8, 2013.
PCT Application PCTUS2014017136—International Search Report and Written Opinion dated Jul. 25, 2014.
PCT Application PCTUS2014023654—International Search Report and Written Opinion dated Aug. 7, 2014.
PCT Application PCTUS2014051008—International Search Report and Written Opinion dated Nov. 20, 2014.
PCT Application PCTUS2014051008—Preliminary Report on Patentability dated Mar. 1, 2016.
"CAD and CAM—possibilities of optimization in total prosthetics (I)", QUINTESSENZ, Becker, Apr. 1991, Issue 4, p. 397 to 404.
"Geroprosthetics: Age-appropriate prosthesis design with heart and mind," ZTM AKTUELL, Maas, Jul. 2010.
N. Savic, PalaDigtal.com, "My Digital Denture," Supplement to Inside Dental Technology magazine, Aegis Communications, Mar. 2017.
Baltic Denture System product information printed on May 15, 2017 from AvaDent website; posting date unknown.
AvaDent product information printed on May 15, 2017 from Avadent website; posting date unknown.
Morales et al., "A Digital Spin on Traditional Dentures," Chairside Magazine, vol. 11, Issue 4, Glidewell Laboratories, Mar. 27, 2017.
Han, Wei li et al., "Design and fabrication of complete dentures using CAD/CAM technology.", Medicine vol. 96, 1 (2017): e5435.
U.S. Appl. No. 14/195,348—Notice of Allowance dated Nov. 30, 2018.
U.S. Appl. No. 14/195,348—Notice of Allowance dated Jan. 18, 2019.
U.S. Appl. No. 14/506,338—Notice of Allowance dated Oct. 17, 2018.
U.S. Appl. No. 15/152,521—Restriction Requirement dated Aug. 21, 2017.
U.S. Appl. No. 15/152,521—Non-Final Office Action dated Apr. 2, 2018.
U.S. Appl. No. 15/152,521—Non-Final Office Action dated Nov. 29, 2019.
U.S. Appl. No. 15/284,481—Restriction Requirement dated Dec. 28, 2017.
U.S. Appl. No. 15/284,481—Non-Final Office Action dated Sep. 26, 2018.
U.S. Appl. No. 15/697,695—Non-Final Office Action dated Jul. 30, 2019.

* cited by examiner

SYSTEMS AND PROCESSES FOR FORMING ANATOMICAL FEATURES IN DENTURES

CROSS-REFERENCE TO RELATED APPLICATIONS

This application is a Continuation of, and claims priority to and the benefit of, U.S. patent application Ser. No. 13/823,621 filed on Mar. 14, 2013, and entitled "SYSTEMS AND PROCESSES FOR FORMING ANATOMICAL FEATURES IN DENTURES" and PCT Application Serial No. PCT/US11/59230 filed Nov. 3, 2011, and entitled "SYSTEMS AND PROCESS FOR FORMING ANATOMICAL FEATURES IN DENTURES"; and U.S. patent application Ser. No. 12/939,138 filed Nov. 3, 2010, and entitled SYSTEMS AND PROCESSES FOR FORMING ANATOMICAL FEATURES IN DENTURES, each aforementioned application is incorporated by reference in its entirety for all purposes.

FIELD OF THE INVENTION

This invention relates to the field of manufacturing of dentures and particularly forming anatomical and functional features in dentures.

BACKGROUND OF THE INVENTION

Dentures need to be closely fitted to anatomical landmarks on the patient in order for the denture to comfortably fit as well as to be under the neuromuscular control of the patient. It is critical for the dentures to properly fit in order for the dentures to be worn comfortably and securely without the embarrassment of falling out during use.

The anatomical landmarks are typically located relative to the patient's anatomy by using a customized denture impression tray. Thermoplastic molding compound is applied along the peripheral edges of the tray which is positioned in the patient while the compound is soft. The patient manipulates their jaw while the compound is setting to provide in the impression appropriate clearances within the buccal, labial and/or lingual folds. This process is uncomfortable for the patient and does not provide precise location of the anatomical features. The resulting impressions are typically used in creating a wax rim. The wax rim is tried in the patient and marked to provide areas which need to be carved for a better fit. This requires skill on the part of the dentist and technicians.

One critical area of fit for the denture is the post dam. The post dam on a denture is a ridge along the back of the denture which presses slightly into the posterior palate to form a seal. The increased thickness of the denture along a narrow border adds pressure on the tissue and maintains a vacuum seal. Without this sealing effect, the upper denture the vacuum between the denture and the roof of the mouth is reduced or lost and the denture loosens as the wearer talks, chews or swallows. This seal is critical for the upper denture to be secure in the patient.

The ideal location for the post dam is along the junction of the hard and soft palates. The junction between the hard and soft palate where the denture border lies is neither a straight line nor of uniform consistency. It is harder in the midline and soft on both sides of the midline. Thus, an ideal post dam has to reflect the anatomy and features of that part of the mouth. If the denture extends too far to the rear of the mouth, the patient may suffer from gagging. If the denture extends too much into the hard palate, the denture will likely lose the vacuum seal and will not fit.

Currently, the post dam is created on the denture by modifying the impressions or by application of a wax material to the area of the plaster model representing the roof of the mouth. Both require the use of a plaster model of the denture upon which the post dam is carved by a technician based on the estimation of where the line between the hard and soft palate occurs in the impression into the mold from the denture will be fabricated. Both techniques are less than precise in locating the ideal position. Thus the precision on where the post dam is located depends upon the quality of the impressions and the skill of the technician.

Another set of anatomical feature that are critical for the proper use of dentures are the labial and buccal frenae. The labial frenum attaches to the center of the upper lip and between the upper two front teeth while the buccal frenums attach the alveolar ridge to the cheek on each side of the mouth. If the matching notches of the denture are not located precisely for the labial frenum and the buccal frenums, the denture can often be pulled loose. Currently these frenums are visually located by the dentist or technician and the notches formed by a file in the impressions.

The rugae is typically neglected in the creation of dentures. The palatial rugae is asymmetrical and has irregular elevations of the mucosa located in the anterior third of the palate. Each individual has a unique rugae which can affect the speech of the individual. Currently, most dentures do not include a rugae and are smooth, instead. In those instances where a denture does include a rugae, the rugae is typically formed from a template rather than having a unique rugae for each patient.

Thus, presently there is no process for creating dentures that have the precise fit to or mimicking of the anatomical features of the patients mouth.

SUMMARY OF THE INVENTION

The present invention provides systems and processes for creating dentures that have features precisely located and formed to provide a close comfortable fit for the dentures in the patient. These features provide critical functional and aesthetic improvement for the fit and comfort of the patient. The system of a preferred embodiment uses a process whereby a true replication of the patient's jaw structure is created in a digital three dimensional model. This true replication is then used to precisely locate and/or copy the anatomical landmarks of the patient for use in fabricating a denture base for use in a denture for the individual patient.

The term denture base generally refers to the part of a denture that fits the oral mucosa of the basal seat, restores the normal contours of the soft tissues of the edentulous mouth, and supports the artificial teeth. The term denture refers to the denture base with the artificial teeth attached. The term anatomical landmarks refers to the structures on the anatomy of the wearer that define the periphery of the denture. The term anatomical features includes the features corresponding to the anatomical landmarks of the wearer as well as aesthetic and functional features that are created in the denture.

One anatomical landmark that is determined preferably by the system, but alternatively by a technician using the system is the line between the hard and soft palates. This line is irregular and difficult to determine precisely using current techniques. One preferred embodiment of the present invention determines this line from the digital model. Once this line is determined, a post dam is created on the digital model.

Another set of anatomical landmarks that are determined are the labial frenum and the buccal frenums. The precise location of the frenums in a preferred embodiment is identified so that notches matching these frenums are precisely located and shaped in the denture base. This minimizes dislocation of the denture during speech and improves the comfort, fit and aesthetics of the denture.

Another preferred embodiment accentuates the buccal reflection of the patient. This accentuation is called the buccal roll. The buccal roll for purposes of this patent is defined as the small rounded ridge that is added to the denture to improve vacuum adherence, goes from the anterior middle back to the most posterior points on the outer margin. From this precise location of the buccal roll, a slight undercut can be formed in the denture base. The tissues and muscles surrounding the buccal roll will engage into the undercut to form a gripping region to further secure the denture.

The system of a preferred embodiment is able to precisely locate the margin, or trim line along the buccal reflection. This reduces the time for technician to carve or trim the denture base after molding and improves the comfort. This line can also be registered by the system to be included into the digital denture model and on the denture base.

Another embodiment of the present invention determines the soft tissue lines from the digital model so that they can be registered and included into the denture base for fabrication. In particular, the gingival margin where the gum ends on the teeth and the soft tissue surrounding the roots of the teeth below the gum are mimicked on the denture base. These soft tissue lines are largely for aesthetic reasons but also may improve the comfort to the patient.

One unique feature of a preferred embodiment is able to create the rugae of the individual patient for use in the denture base. The rugae is copied on the tissue side and mimicked on the teeth side. The rugae can also be accentuated or diminished as needed to improve the speech or comfort of the patient. Each rugae is unique to an individual and affect the speech and comfort of the individual. The rugae is also used to identify individuals for forensic purposes. The rugae is registered by the system for copying into the digital denture base model for selection or fabrication in the denture base.

The system of a preferred embodiment may also be used to select areas of the denture base that may be selectively thinned or thickened. This thinning or thickening may be done across the arch of the denture base, along the palatial region of the denture base or around the teeth pockets. The system or a user of the system is able to identify areas on the digital model that may be able to be thinner without jeopardizing structural integrity. The system can perform finite element analysis or other design on the fly techniques to determine the optimum design for the denture base and the denture teeth.

In a preferred embodiment, once the anatomical (including aesthetic and functional features) have been formed in the digital denture model, the denture teeth are selected or fabricated, the denture base is fabricated. The teeth are temporarily installed in the denture base to create a try-in denture. The try-in denture is then shipped to the dentist for a patient try-in. If the fit is not satisfactory, then the denture is used as a secondary impression tray and new impressions are created and scanned. These scans along with any additional changes in measurement data are put back into the system to render an improved digital denture model. New denture teeth are selected or fabricated based on this improved model, if necessary. The teeth are once again temporarily installed and the improved try-in denture is ready for another try-in with the patient.

The system of a preferred embodiment may also be to select and design areas where implant supports may be placed. These implant supports could be for example a bar or housing. The placement could be a optimization process between the anatomical landmarks captured by a CT scan (bone density and shape) and the aesthetics and functional aspects of the denture.

This process is continued until the patient and dentist are satisfied with the denture. Once the denture has been deemed satisfactory, the denture is shipped back to the lab so that the teeth can be permanently installed and the final finish and polish procedures are performed. The finished denture is then shipped to the dentist for the patient final insert and acceptance.

These and other features of the claimed inventions will be evident from the ensuing detailed description of preferred embodiments, from the drawings and from the claims.

DETAILED DESCRIPTION

The present invention provides systems and process for the fabrication of dentures that correspond to anatomical landmarks of the patient. Descriptive embodiments are provided before for explanatory purposes. It is to be expressly understood that the present invention is not be limited to these descriptive embodiments. Other embodiments are considered to be within the scope of the present invention, including without limitation the use of the present invention for other applications, such as denture duplication, dental implants, and other dental and orthodontic applications. The descriptions below discuss the systems of the present invention as used in dental labs, but it is to be expressly understood that these systems could also be implemented in the dentist office or through a network allowing interaction between the dentist and the dental lab through the systems. The processes and systems of the present invention may also be used in combination with all or parts of the following co pending applications filed on Nov. 3, 2010, entitled System and Process for Optimization for Dentures, Ser. No. 13/823, 662; System and Process for Duplication of Dentures, Ser. No. 13/823,466; Combination Tool for Measuring Dental Anatomical Features, Ser. No. 13/249,910; and Removable Tool for Denture Uses, Ser. No. 12/939,143; all of which are hereby incorporated herein by reference.

Overview

The terms denture base generally refers to the part of a denture that fits the oral mucosa of the basal seat, restores the normal contours of the soft tissues of the dentulous mouth, and supports the artificial teeth. The term denture refers to the denture base with the artificial teeth attached. The term anatomical landmarks refers to the structures on the anatomy of the wearer that define the periphery of the denture. The term anatomical features includes the features corresponding to the anatomical landmarks of the wearer as well as functional and aesthetic features that are created in the denture.

The system of a preferred embodiment uses a process whereby a true replication of the patient's jaw structure is created in a digital three dimensional model. This true replication is then used to precisely locate and/or copy the anatomical landmarks of the patient for use in fabricating a denture base for use in a denture for the individual patient.

Figure 1:
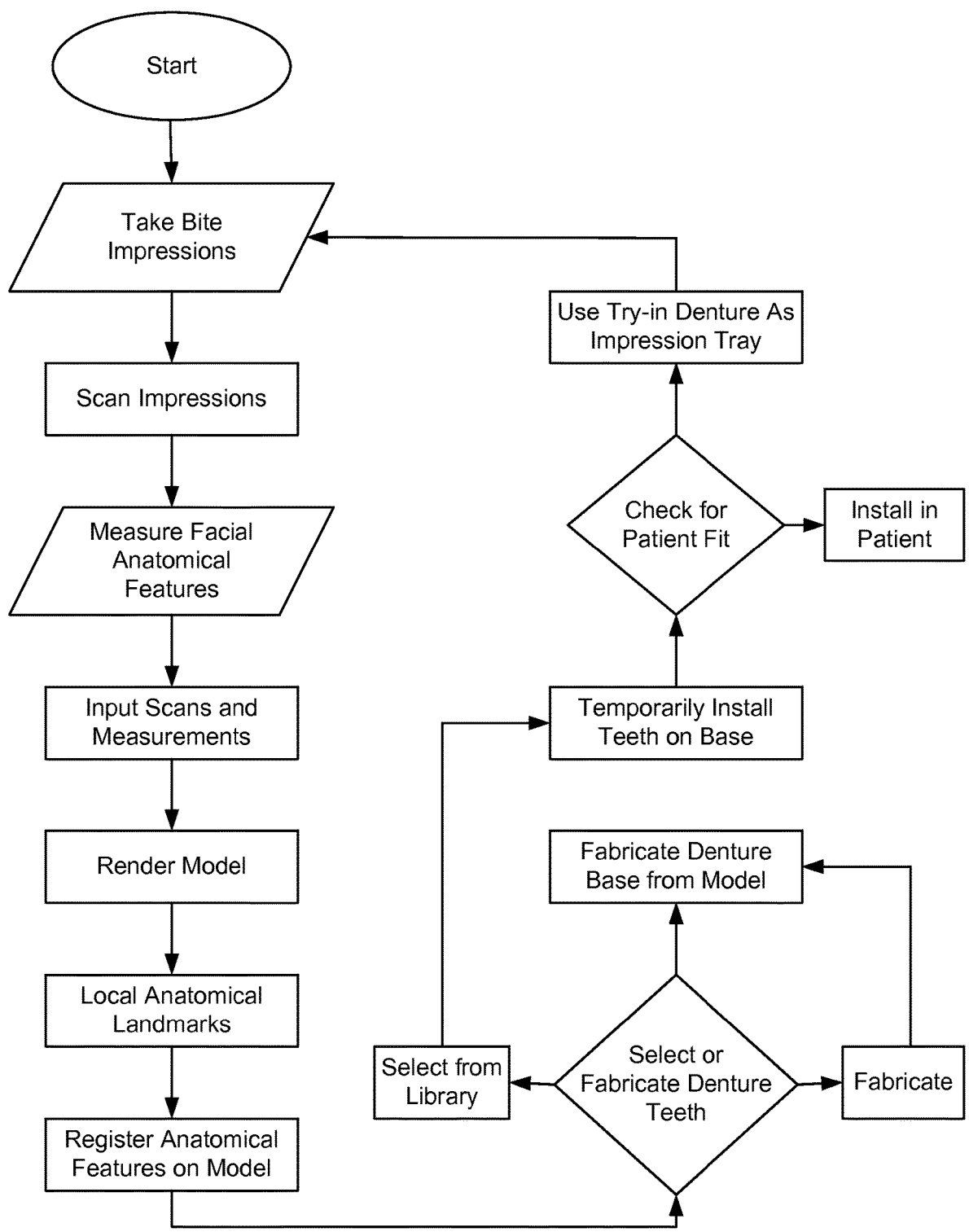
FIG. 1 illustrates a workflow diagram of an embodiment of the present invention.

In one preferred embodiment as described in the flow chart of FIG. 1, cans of the patient's bite impressions are taken and a number of measurements from the patient on their initial visit. These measurements are based on the anatomical features of the patient. The dentist may also provide information regarding to the selection of the teeth. This information is transmitted to the dental lab where the system creates a digital three dimensional model of the patient's jaw structure from the scans and from the measurements. It is to be expressly understood that other methods of creating a digital three dimensional model of the jaw structure may be used as well. The process described herein is only one embodiment for doing so.

Once the digital model has been created, denture teeth are selected from a library or fabricated directly for that digital model. This can be based on using a library and selecting the best denture teeth, through an optimization process as described in the above identified co pending application, or through another process.

The system of a preferred embodiment of the present invention either creates a digital denture base or modifies an existing digital denture base to create the best fit in the patient by precise use of the anatomical landmarks of the patient. These include locating the ideal location of the post dam, locating and forming the notches for the labial and buccal frenums, creating the idealized margins along the buccal reflection, creating the idealized gum line and root structures, creating a true copy of the patient's palatial rugae and duplicating that structure on the denture base, locating the soft tissue lines of the patients mouth, locating areas for dental implant structures and any other features that are useful or desirable from either a functional or aesthetic standpoint.

A description of one process and system for preforming the claimed inventions is described below. In this preferred embodiment, a digital three dimensional model of the patient's mouth and jaw structure is created from scanned bite impressions and from precise measurements of the anatomical features of the patient.

Measurement Process

Figure 2:
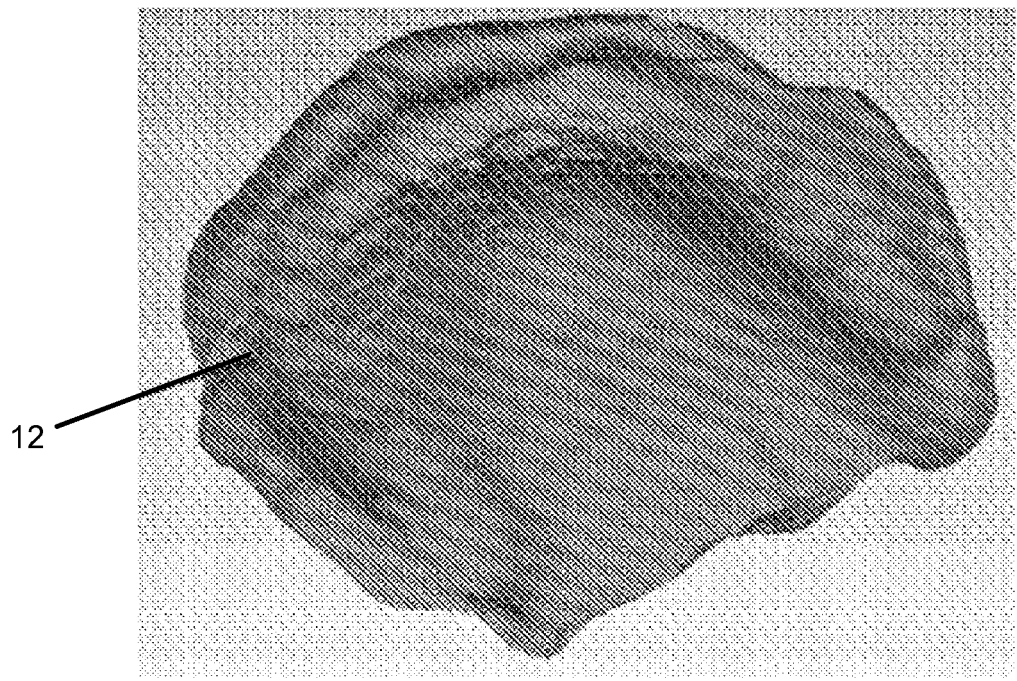
FIG. 2 is an inner and outer scan of a bite impression.

The dentist obtains data regarding several anatomical landmarks of the patient to send to the dental lab. First, the dentist takes the bite impressions. This can be done by using an upper bite impression tray, a lower bite impression tray and a centric relationship tray or a triple bite impression tray that simultaneously takes upper and lower and centric bite impressions. The resulting bite impressions are digitally scanned as shown in FIG. 2 and transmitted to the lab or directly into the system. The bite impressions provide the bite registration, the prepared area and the opposing teeth. Alternatively, or in conjunction with this process, an intraoral digital scanning may be done.

The dentist also takes additional measurements of anatomical features of the patient. These include, without limitation, the vertical height relation to the upper and lower bite alignment; the lip support of the patient; the smile line of the patient; the centric relationship of the patient; and the midline measurement. Other measurements may be taken as well.

The lip line measurement is intended to provide a measurement of the upper lip from the anterior papilla at rest. This is traditionally measured by a papillameter which consist of a vestibule shield, incisive papilla rest and an vertical handle with measurement increments.

The smile line measurement can also be determined by the papillameter. The device is inserted into position and the patient is requested to smile so that the lip line at that position from the anterior papilla can be measured.

The midline is determined from typically from the existing intraoral anatomic structures, usually the maxillary anterior labial frenum.

The vertical height dimension is typically determined from measurements taken from nose and chin reference points. Measurements of the vertical height are taken at rest and of the vertical dimension of occlusion.

A centric tray is commonly used to take a double arch registration to record vertical and centric jaw registration.

The occlusal plane is an orientation of the position of an imaginary occlusal plane which theoretically touches the incisal edges of the incisors and tips of the occluding surface of the posterior teeth. A normal occlusal plane extends parallel to a line drawn from the tragus of the ear to the ala of the nose and parallel to the interpupillary line (Kamper's Line). This ensures that the patient will not dislodge the lower denture, particularly while eating and not bite the lateral borders of the tongue. Tools for measuring the occlusal plane typically include a thin flat plane have a curved bite piece and a pair of laterally and distally extending wings projecting from the bite piece.

There are individual tools for each of these measurements. A single tool for obtaining all of these measurements is disclosed in co-pending application Ser. No. 14/798,717 and is incorporated by herein above. In a preferred embodiment of the present invention, this tool is used to supply the necessary measurements for the optimization process for designing a denture mold.

The dentist also selects the teeth to be fitted into the denture base. Typically, the dentist will use a facial meter, anterior tooth selection guide and a library catalog to determine the appropriate teeth. Other methods may be used as well along with the determination of the appropriate shading of the teeth.

The scan, measurements and teeth selection are then transmitted to the dental lab or directly into the system.

System

Figure 3:
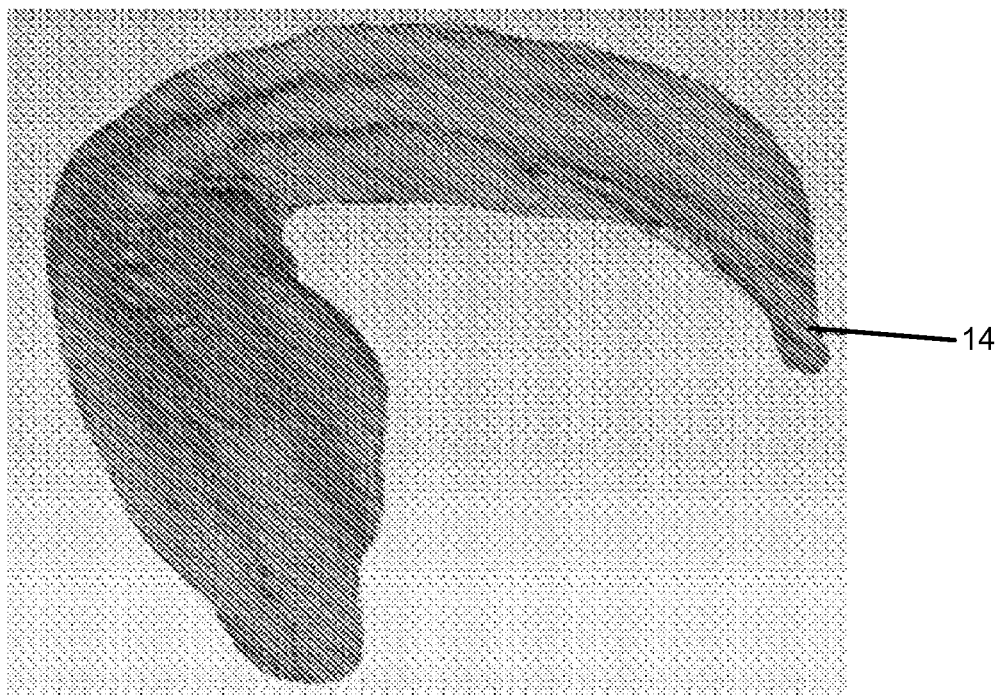
FIG. 3 is a rendition of a three dimensional model of a denture base.

The scanned images 12, 14 of the bite impressions and the measurements are then transmitted into a system that will process this information to create the digital three dimensional model. Systems for creating such digital three dimensional models are disclosed in U.S. Pat. No. 6,616,444, assigned to Ormco Corporation and patents relating to that patent, U.S. Pat. No. 6,851,949, assigned to OraMetrix, Inc. and patents relating to that patent; and U.S. Pat. No. 7,433,810, assigned to Align Technology, Inc. and patents relating to that patent, all of the above cited patents and patents and published patent applications relating to them are incorporated herein by reference. These systems are disclosed for use with orthodontic appliances. The present invention takes the information from these systems and utilizes the additional information described above in regard to the measurements of the patient's anatomy and impressions to create a digital model 20 as shown in FIG. 3 for use with creating and optimizing a denture base.

Figure 4:
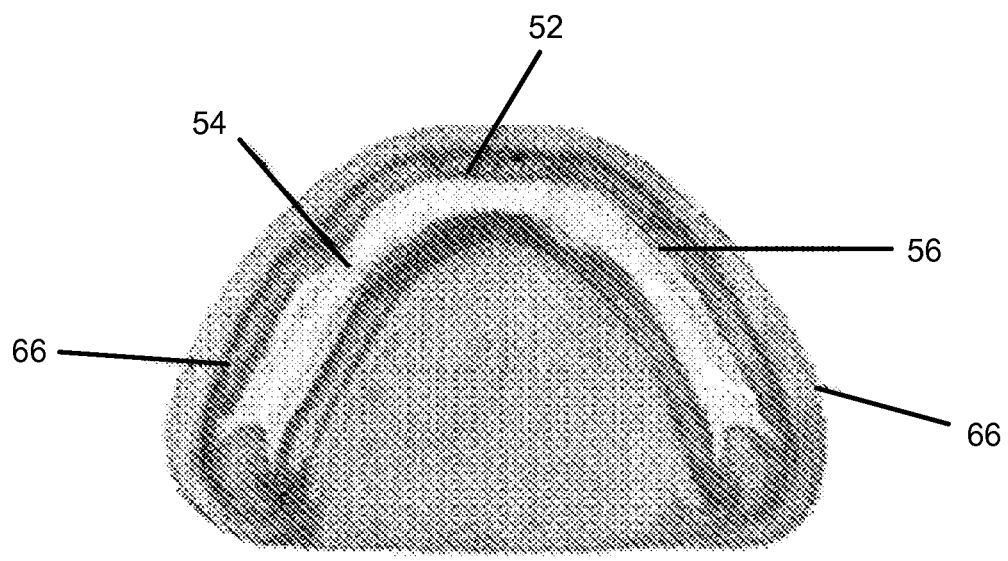
FIG. 4 is an illustration of the mandibular arch

The system of a preferred embodiment further includes the capability to uniquely distinguish certain anatomical landmarks of the patient from this digital model. These landmarks are used to create features that are registered to ensue their incorporation into the digital model of a denture base from which a denture base is fabricated. The anatomical landmarks of the mandibular arch, as shown in FIG. 4 and of the maxillary arch as shown in FIG. 5 are critical for the proper fit of the denture.

Figure 5:
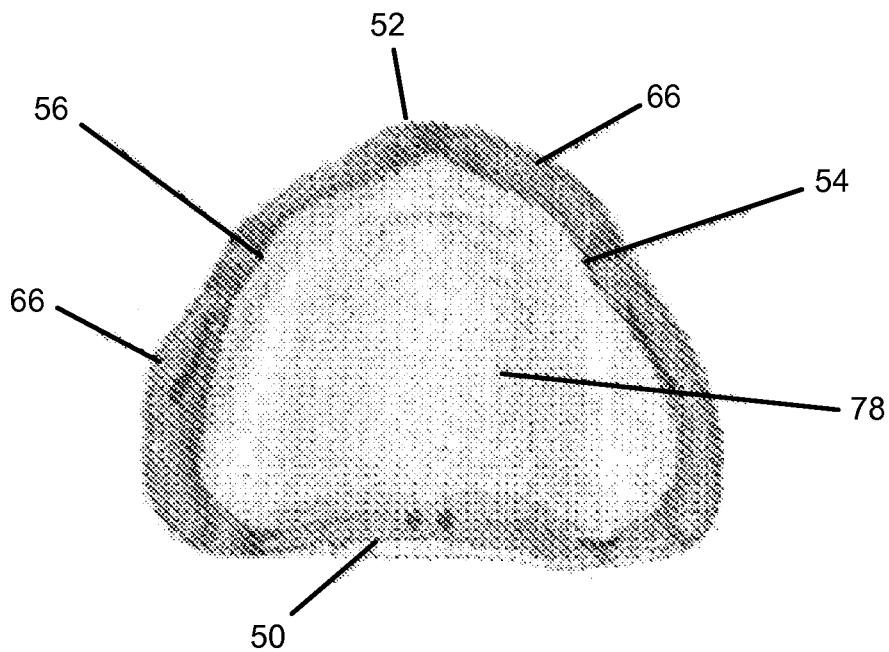
FIG. 5 is an illustration of the maxillary arch.
Figure 6:
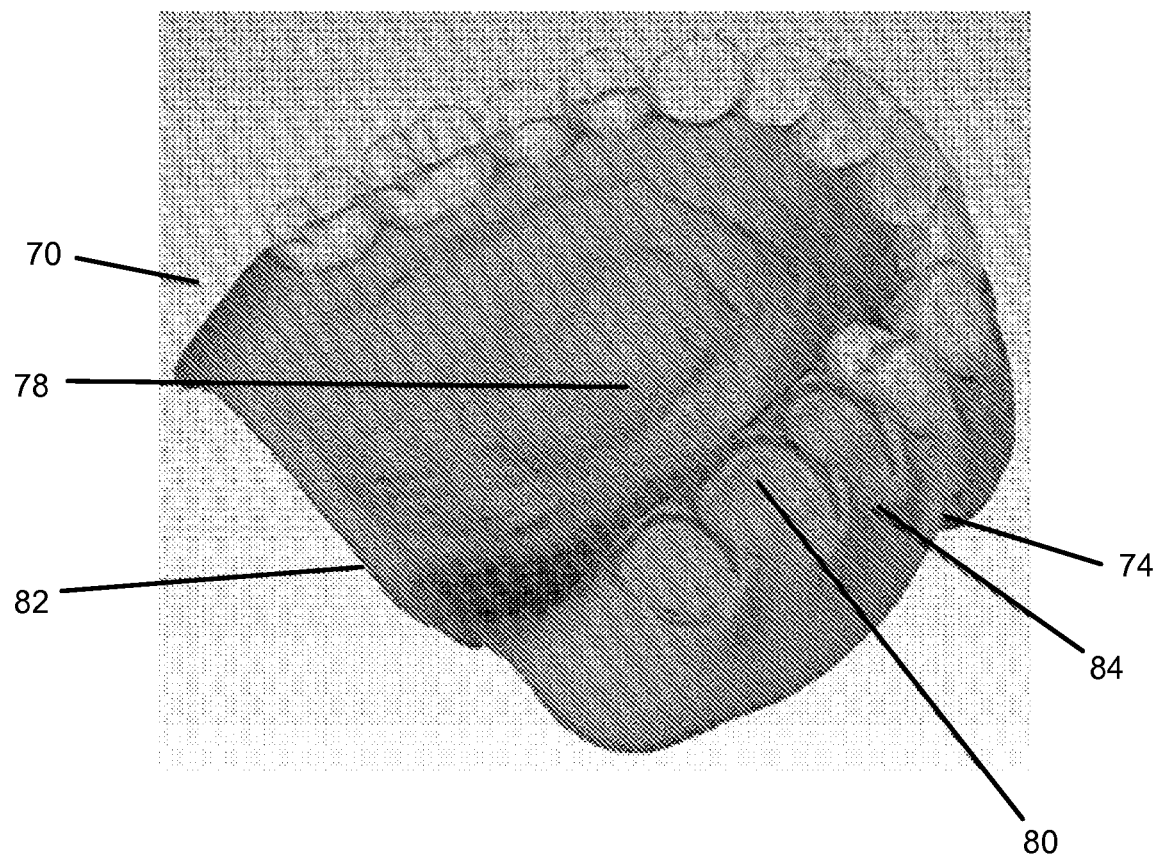
FIG. 6 is an illustration of a rear perspective view of a denture base of a preferred embodiment of the present invention.

One anatomical landmark that is determined preferably by the system, but alternatively by a technician using the system is the line 50 as shown in FIG. 5 between the hard and soft palates. This line is irregular and difficult to determine precisely using current techniques. This line can be determined from the digital model based on the pressure or density in which the bite impressions are formed. For example, the impression will have a greater density at the hard palate due to the greater pressure applied upon it compared to the pressure exerted by the soft palate when the patient bites down on the impression compound. The line may also be readily noticeable simply due to this change in pressure between the palates on the impression compound. This can show up as different colors on the digital model or simply be registered by the system. Other techniques may be used as well. The system then is able to create the post dam along that line of demarcation. This will ensure a tight seal to create a vacuum between the denture and palate to secure the denture.

Figure 7:
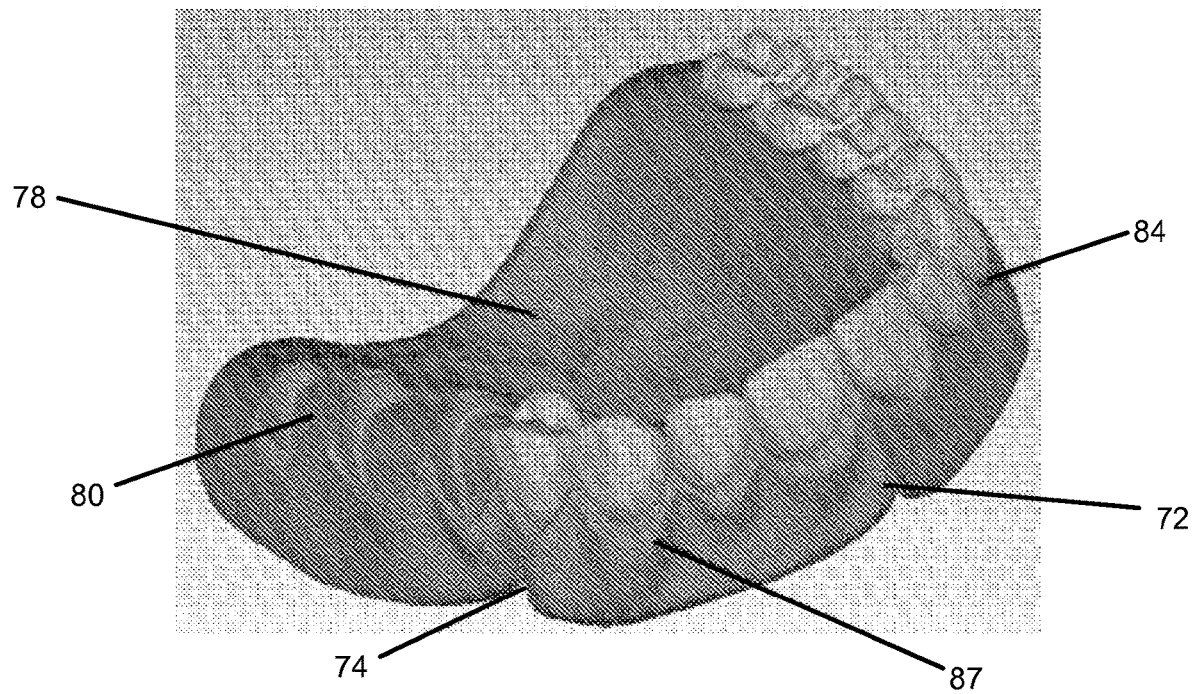
FIG. 7 is a front perspective view of the denture base.
Figure 8:
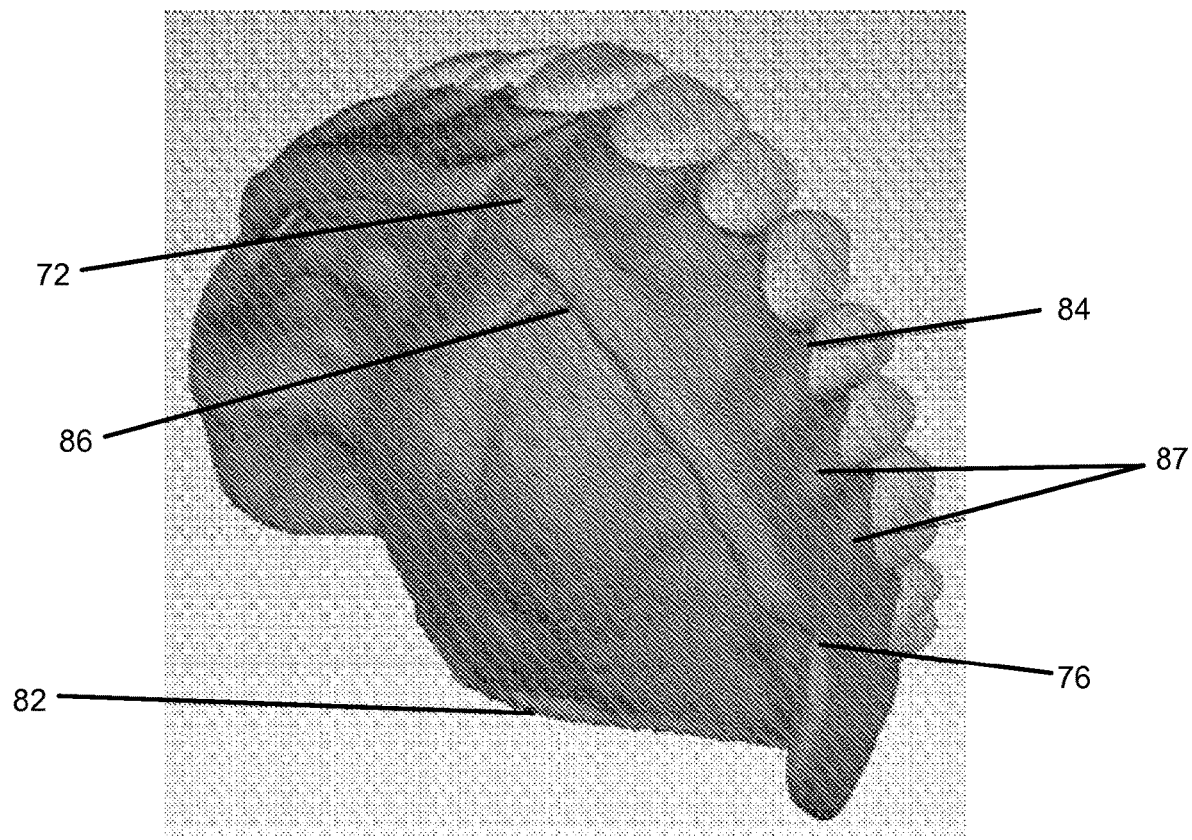
FIG. 8 is top perspective view of the denture base.
Figure 9:
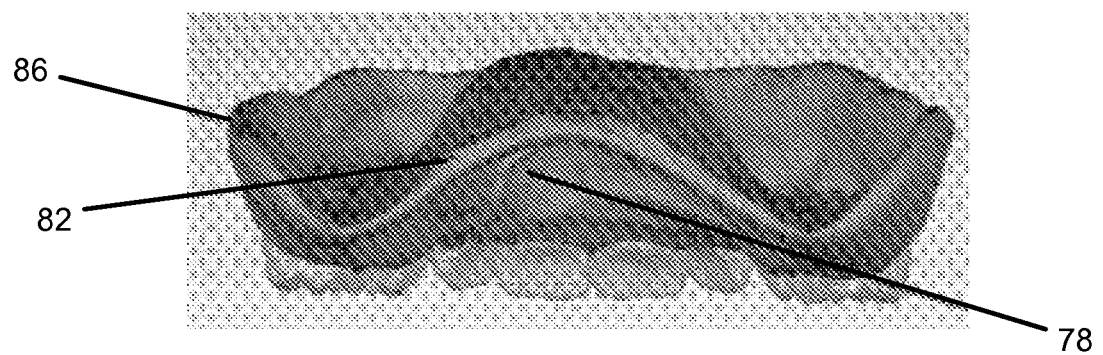
FIG. 9 is a rear view of the denture base.

Another anatomical landmark that is determined is the labial frenum 52. The precise location of the labial frenum can be registered for the creation of the notch 72 as shown in FIG. 7. The buccal frenums 54, 56 are also located and registered to create notches 74, 76 in the denture base for these frenums as well. This minimizes dislocation of the denture during speech and improves the comfort, fit and aesthetics of the denture.

The buccal reflection 66 of the patient can be located as well by changes in density due to changes in pressure on the impression compound or simply by the change in structure of the impression. From this precise location of the buccal reflection, the buccal roll 59 can be formed on the denture base. Then, an undercut can be formed in the denture base on the buccal roll. The tissue and muscles surrounding the buccal roll will engage into the undercut to form a gripping region to further secure the denture.

The margin, or trim line along the buccal reflection 66, as shown in FIG. 4 can be precisely located. This reduces the time for technician to carve or trim the denture base after molding and improves the comfort. This margin line can also be registered by the system to be included into the digital denture base and denture base.

The soft tissue lines are also determined from the digital model so that they can be registered and included into the denture base for fabricating the base. In particular, the gingival margin where the gum ends on the teeth and the soft tissue surrounding the roots of the teeth below the gum are mimicked on the denture base. These soft tissue lines are largely for aesthetic reasons but also may improve the comfort to the patient.

The rugae 78 of the individual patient can also be uniquely copied for use in the denture base. Each rugae is unique to an individual and affect the speech and comfort of the individual. The rugae is also used to identify individuals for forensic purposes. The rugae is copied on the tissue side and mimicked on the teeth side. The rugae can also be accentuated or diminished as needed to improve the speech or comfort of the patient. The rugae is registered by the system for copying into the digital denture base.

Figure 11:
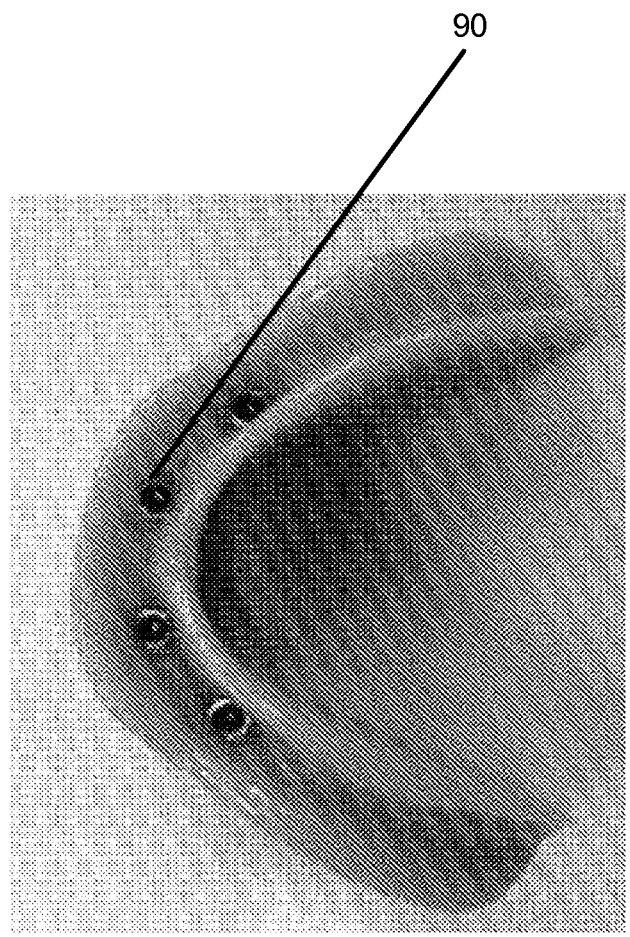
FIG. 11 is an illustration of a denture base with implant housings.

The digital denture model can also be used to identify locations on the optimal denture base for implant supports to be inserted. These supports can be housings such as housings 90 shown in FIG. 11 or bars or other types of supports.

The digital denture model can also be used to identify areas on the denture base which can be thinned to increase comfort while not compromising the structural integrity of the denture base. This can be in the arch, the palatial region and around the teeth pockets. A finite element analysis can also be used to determine these areas.

Other features can be identified and registered by the system if desired. In one embodiment, denture teeth are selected from a library that best fits the digital denture base and modified if necessary. In an alternative embodiment, the denture teeth are fabricated directly from information based on the digital denture base model.

Figure 10:
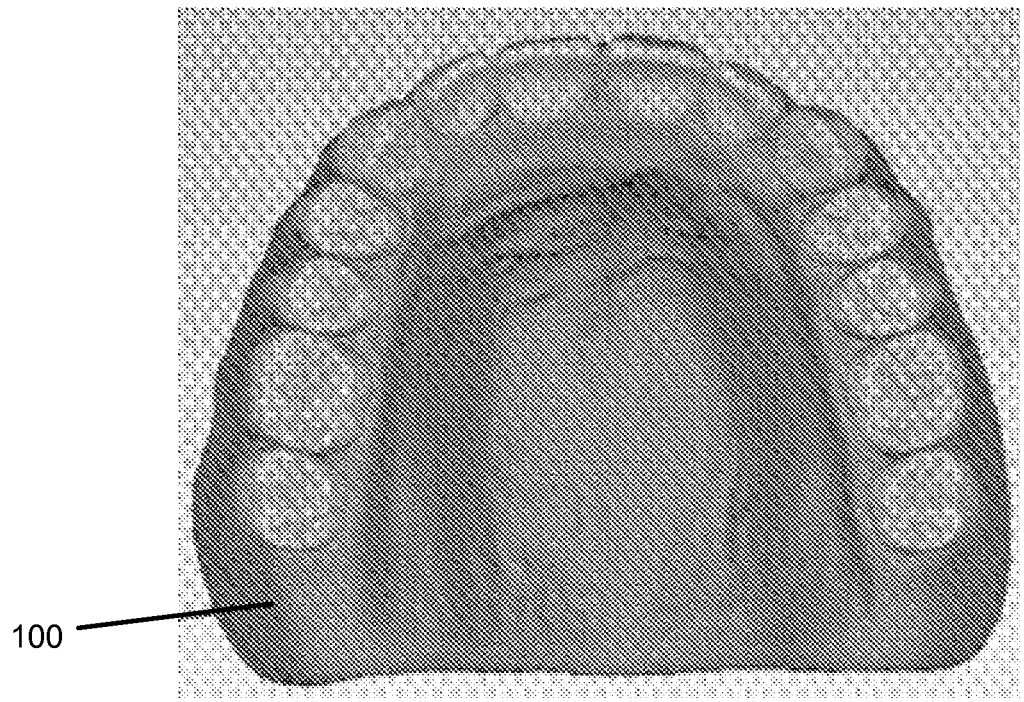
FIG. 10 is a top view of the lower denture base.

Examples of a denture base with the features formed therein are illustrated in FIGS. 6-11. Denture base 70 includes a notch 72 for the labial frenum as well as notches 74, 76 for the buccal frenum. A true rugae 78 that mirrors the patient's rugae is formed as well. Pockets 80 are formed, preferably by milling or rapid prototyping, for the installation of the teeth. The geometry of these pockets has been critically designed for the best occlusal fit of the teeth. Post dam 82 has been formed precisely along the line of between the hard and soft palate. The margins or gum lines 84 and root structures 87 have also been created as well. Critical areas have also been selected to thin the denture base, particularly along the arch palate and teeth pockets. An buccal roll 86 in FIG. 8 may also be formed for engagement along the buccal reflection 66 as well. A lower denture 100 is also shown in FIG. 10.

The denture base is selected or fabricated and the teeth are temporarily installed. This try-in denture is then shipped to the dentist for a patient try-in. If the fit is not satisfactory, then the denture is used as a secondary impression tray and a new impression is created and scanned. This scan along with any additional changes in measurement data is put back into the system. A new denture base is created. The teeth are once again temporarily installed and the denture is ready for another try-in with the patient.

This process is continued until the patient and dentist are satisfied with the denture. Once the denture has been deemed satisfactory, the denture is shipped back to the lab so that the teeth can be permanently installed and the final finish and polish procedures are performed. The finished denture is then shipped to the dentist for the patient final try-in and acceptance.

The system of a preferred embodiment of the present invention can be implemented in many forms. The above description below is simply one example of an implementation of the system.

It is to be expressly understood that the above description is intended only for explanatory purposes and is not meant to limit the scope of the claimed inventions. Other embodiments are considered to be within the scope of the claimed inventions.

The invention claimed is:

1. A computer-implemented method for creating anatomical features in a denture, the method comprising:
creating a three dimensional digital model of the mouth and jaw structure of a patient; identifying anatomical landmarks of the patient on the digital model via a software system or a user of the software system, the step of identifying anatomical landmarks selected from the group comprising identifying a labial frenum or identifying a buccal frenum;
creating a digital model of a denture base that includes anatomical features based upon the anatomical landmarks, wherein the anatomical features is selected from a group comprising of a notch based upon the labial frenum or a notch based upon the buccal frenum; and
fabricating a denture base that corresponds to the digital model of the denture base; wherein said step of identifying the anatomical landmarks includes: identifying the buccal reflection; and the step of creating a digital model of a denture base that includes the identified anatomical landmarks further comprises creating an undercut adjacent a buccal roll corresponding to the buccal reflection.

2. The method of claim 1 wherein said step of identifying the anatomical landmarks includes: identifying a line between the hard and soft palates; and the step of creating a digital model of a denture base that includes the anatomical features further comprises creating a post dam on the denture base model.

3. The method of claim 1 wherein said step of identifying the anatomical landmarks includes: identifying a trim line; and the step of creating a digital model of a denture base that includes the identified anatomical landmarks further comprises creating a margin or trim line along a buccal reflection.

4. The method of claim 1 wherein said step of identifying the anatomical landmarks includes: identifying rugae; and the step of creating a digital model of a denture base that includes the identified anatomical landmarks further comprises creating a true rugae on the digital model.

5. The method of claim 1 wherein said step of identifying the anatomical landmarks includes: identifying areas for thinning on the digital model of the denture base; and the step of creating a digital model of a denture base that further comprises the identified anatomical landmarks includes selectively thinning the denture base on the digital model of the denture base.

6. The method of claim 1 wherein said step of identifying the anatomical landmarks includes: identifying areas of soft tissue around the teeth of the digital model; and the step of creating a digital model of a denture base that includes the identified anatomical landmarks further comprises creating soft tissue lines around a gum line around the teeth to simulate roots of the tooth.

7. The method of claim 1 wherein said step of identifying the anatomical landmarks includes: identifying areas for placement of implant supports on the digital model; and the step of creating a digital model of a denture base that includes the identified anatomical landmarks further comprises locations for implant-supports on the digital model.

* * * * *